United States Patent [19]

Pershadsingh

[11] Patent Number: 5,981,586
[45] Date of Patent: Nov. 9, 1999

[54] METHODS FOR TREATING PROLIFERATIVE AND INFLAMMATORY SKIN DISEASES

[76] Inventor: Harrihar A. Pershadsingh, 404 Windsor Park Dr., Bakersfield, Calif. 93311

[21] Appl. No.: 09/084,037

[22] Filed: May 22, 1998

Related U.S. Application Data

[60] Provisional application No. 60/047,550, May 23, 1997.

[51] Int. Cl.$^6$ .......................... A61K 31/235; A61K 31/19
[52] U.S. Cl. .............................................. 514/543; 514/571
[58] Field of Search ..................................... 514/543, 571

[56] References Cited

FOREIGN PATENT DOCUMENTS

WO
9535108A1  12/1995  WIPO.

WO
9609055A1  6/1996  WIPO.

OTHER PUBLICATIONS

Cunliffe et al—Brit. J. Dermatol. 81 (X), 280–2 (Abstract), 1969.

*Primary Examiner*—Raymond Henley, III
*Attorney, Agent, or Firm*—Townsend and Townsend and Crew LLP

[57] ABSTRACT

Methods of inhibiting the proliferation of keratinocytes and inflammation of the skin comprising administering to a human in need of treatment an effective amount of a compound that modifies the activity of the peroxisome proliferator activated receptor gamma (PPARγ) in skin; and pharmaceutically acceptable salts and solvates thereof.

6 Claims, 5 Drawing Sheets

METHODS FOR TREATING PROLIFERATIVE AND INFLAMMATORY SKIN DISEASES

This is a continuation-in-part of U.S. provisional patent application Ser. No. 60/047,550, filed May 23, 1997.

BACKGROUND OF THE INVENTION

1. Field of the Invention

This invention relates to hyperproliferative and inflammatory disorders of the skin, especially to new methods for inhibiting proliferation of keratinocytes and for treating hyperproliferative and inflammatory disorders of the skin including psoriasis and acne vulgaris.

2. Background

Abnormal cell proliferation and inflammation are key features of a number of disorders of the skin. For example, hyperproliferation of keratinocytes is a key feature of psoriasis, a disease of the skin which produces inflammatory lesions that are thickened, scaling, and non-scarring. Psoriasis affects about 1–2% of the United States population with an incidence of about 200,000 new cases per year. Hyperproliferation of keratinocytes and inflammation of the skin are also key features of acne vulgaris, a disorder that produces comedones and the potential for scarring lesions and cysts. Acne is a very common disorder particularly among teenagers. For example, acne has been reported to affect as many 35 percent of males and 41 percent of females between the ages of 15 and 19.

Nuclear hormone receptors are intracellular receptors that influence the expression of genes involved in cell proliferation and inflammation. Nuclear hormone receptors present in skin play a key role in the proliferative and inflammatory changes that contribute to psoriasis, acne vulgaris, and other hyperproliferative and inflammatory disorders of the skin. Examples of nuclear hormone receptors known to be present in skin include the vitamin D receptor, the retinoic acid receptor, and the steroid receptor.

It has been reported that some nuclear hormone receptors are not expressed in mammalian skin. For example, the prior art indicates that mammalian keratinocytes do not express any nucleic acid message encoding the peroxisome proliferator activated receptor gamma (PPARγ), a member of the Class II family of nuclear hormone receptors. The term PPARγ is used here and throughout this entire writing to mean either the $\gamma_1$ or $\gamma_2$ subtypes or both.

Compounds that modify the activity of nuclear hormone receptors present in skin are known to be useful for inhibiting proliferation of keratinocytes and treating hyperproliferative and inflammatory disorders of the skin such as psoriasis and acne vulgaris. For example, the retinoic acid receptor is a member of the Class II family of nuclear hormone receptors that is expressed in keratinocytes and plays an important role in cell proliferation and inflammation and various disorders including acne vulgaris and psoriasis. Drugs such as etretinate or all-trans retinoic acid that modify the activity of retinoid receptors have proven to be useful for inhibiting hyperproliferation of keratinocytes and for treatment of a variety of hyperproliferative and inflammatory skin diseases including acne vulgaris and psoriasis.

The vitamin D receptor is a member of the Class II family of nuclear hormone receptors that is also expressed in keratinocytes; drugs that modify the activity of the vitamin D receptor in keratinocytes have also been found to be useful for inhibiting proliferation of keratinocytes and for treating psoriasis. Steroid receptors also belong to the superfamily of nuclear hormone receptors and are expressed in skin. Corticosteroids, when administered systemically or topically, have proven to be useful for treating hyperproliferative and inflammatory disorders of the skin including psoriasis and acne vulgaris.

Because the prior art clearly indicates that PPARγ is not present in mammalian keratinocytes, those skilled in the art would not expect compounds that modify the activity of this nuclear receptor to be useful for inhibiting the proliferation of keratinocytes or for treating hyperproliferative or inflammatory disorders of the skin.

Thiazolidinediones are known to have a variety of cellular effects including modifying calcium channel activity, modifying protein kinase activity, and modifying the activity of the peroxisome proliferator activated receptor gamma in various tissues other than skin. Thiazolidinediones inhibit the proliferation of keratinocytes and are useful for treating psoriasis but these effects are not suspected by those skilled in the art to involve modifying the activity of PPARγ. Because the prior art indicates that PPARγ is not present in mammalian keratinocytes, those skilled in the art would not expect other compounds that modify the activity of this nuclear receptor to be useful for inhibiting the proliferation of keratinocytes or for treating hyperproliferative or inflammatory disorders of the skin.

Although a number of compounds that modify the activity of nuclear hormone receptors present in skin can be used to inhibit proliferation of keratinocytes and to treat hyperproliferative, inflammatory disorders of the skin, they are accompanied by a variety of side effects and are not effective in all patients. For example, retinoids are known to treat ogens and can have a broad range of side effects including irritation of the skin and disturbances in lipid metabolism. Vitamin D compounds can cause hypercalcemia and hypercalciuria and only 25%–50% of patients with psoriasis show substantial clinical improvement in response to therapy with vitamin D compounds. Corticosteroids are often effective in reducing hyperproliferative and inflammatory changes of the skin but chronic topical use of corticosteroids can lead to thinning of the skin, development of resistance to therapy, and loss of efficacy. Oral administration of corticosteroids is associated with a number of serious side effects including adrenal insufficiency, hypertension, osteoporosis, and immunosuppression.

Although other therapies exist for hyperproliferative and inflammatory disorders of the skin that do involve compounds that directly modify activity of nuclear hormone receptors, such alternative therapies are not uniformly effective and are accompanied by a variety of side effects that are at best unpleasant and often dangerous. For instance, tar based therapies are uncomfortable and a nuisance to apply. Immunosuppressants such as methotrexate can predispose to malignancy, cyclosporine can cause renal damage and hypertension, and psoralens and ultraviolet light therapy can increase the risk for cancers of the skin.

Because of the distressing and disfiguring nature of hyperproliferative and inflammatory disorders of the skin including psoriasis and acne vulgaris, as well as the unsatisfactory aspects of current therapies, there is considerable interest in developing new methods of inhibiting proliferation of keratinocytes and treating hyperproliferative and inflammatory disorders of the skin.

SUMMARY OF THE INVENTION

According to this invention, human keratinocytes surprisingly express PPARγ (both the $\gamma_1$ and $\gamma_2$ subtypes), a member of the class 11 subgroup of nuclear hormone receptors. Immunohistochemical analysis using antibody specific for PPARγ demonstrated that human keratinocytes express PPARγ protein. The finding that the nuclear receptor PPARγ is expressed by human keratinocytes is surprising and novel because the prior art specifically indicated that mammalian keratinocytes do not express any nucleic acid message encoding PPARγ protein. Based on the surprising finding of PPARγ in human keratinocytes, the invention provides novel methods for inhibiting proliferation of keratinocytes and for treating or preventing hyperproliferative and inflammatory diseases of the skin including psoriasis and acne vulgaris by administration of effective dosages of compounds that modify the activity of PPARγ. In human keratinocytes in culture, troglitazone, a drug known to modify the activity of PPARγ, caused a dose-dependent inhibition of keratinocyte proliferation.

Compounds that modify the activity of PPARγ in keratinocytes can also be used according to the invention to treat other disorders involving epidermal proliferation or epidermal inflammation. Examples of these disorders include eczema; lupus associated skin lesions; dermatitides such as seborrheic dermatitis and solar dermatitis; keratoses such as seborrheic keratosis, senile keratosis, actinic keratosis, photo-induced keratosis, and keratosis follicularis; keloids and prophylaxis against keloid formation, warts including verruca, condyloma, or condyloma accuminatum, and human papilloma viral (HPV) infections such as venereal warts, leukoplakia; lichen planus; keratitis; skin cancer such as basal cell carcinoma and cutaneous T cell lymphoma.

This invention also provides for proliferation inhibition assays using keratinocytes where the assays are used to screen for specific binding of possible therapeutics for skin to the PPARγ receptor.

DETAILED DESCRIPTION OF THE INVENTION

The current invention involves the discovery that human keratinocytes express PPARγ (both subtypes) and that compounds that modify the activity of PPARγ (either γ$_1$ or γ$_2$ subtypes or both), are useful for inhibiting proliferation of keratinocytes and for treating hyperproliferative and inflammatory disorders of the skin. The methods of treatment provided by this invention are practiced by administering to a human in need a dose of a compound that modifies the activity of PPARγ, or a pharmaceutically acceptable salt or solvate thereof, that is effective to inhibit proliferation of keratinocytes. Definitions.

The term PPARγ is used throughout this entire writing to mean either the γ$_1$ or γ$_2$ subtypes or both. The term "inhibit" is defined to include its usually accepted meaning and includes treating a human subject prophylactically to prevent hyperproliferation of keratinocytes and holding in check and/or treating hyperproliferation of keratinocytes. The present method includes both medical therapeutic and/or prophylactic treatment, as necessary.

The term inhibitor is meant to include any compound that both inhibits proliferation in the assays of example 2.

Fatty acids are a group of organic monobasic acids derived from hydrocarbons by the equivalent of an oxidation of a methyl group. They include saturated and unsaturated forms.

Prostaglandins are $C_{20}$ fatty acids containing a cyclopentane ring formed from arachidonic acid by cyclooxygenase activity.

Thiazolidines are a heterocycle of five members where members 1 and 3 are sulfur and nitrogen respectively. See U.S. Pat No. 5,594,015, which is incorporated herein by reference, for a detailed review of the family of thiazolidine members.

This invention is the discovery of the mechanism underlying the antiproliferative activity of known compounds for treating proliferative skin disease. The mechanism is the activation of the PPARγ receptors in keratinocytes. A large and diverse group of compounds are known to bind and to activate the PPARγ receptors and with the knowledge that the receptor exists in skin cells, new antiproliferative drugs become readily available. It is the intent of this invention to claim the use of activators of PPARγ as inhibitors of skin proliferation disease to the extent they are not presently known to be of use for treating skin diseases.

Both known and novel activators of PPARγ can be readily screened for use as skin therapeutics using the various assays described below. Their useful pharmacology (e.g., dose ranges) are readily ascertained by comparing their bioavailability and potency in the same assays as the prior art compounds known to be of use for treating skin disease.

For example, the biological activity of any prostaglandin is difficult to predict without empirical study. While some prostaglandins have been reported as useful for treating skin problems, the J2 prostaglandins described herein were not previously known to be useful for treating psoriasis. Armed with knowledge that these prostaglandins were able to activate PPARγ, the inventors were able to readily confirm their use as antiproliferative agents for skin disease.

In addition to optimizing the screening of novel agents for skin disease within families of compounds known for treating skin disease, e.g. thiazolidines.

There are families of compounds that are not thiazolidinediones, fatty acids or prostaglandins, known to activate PPARγ. The use of these compounds are useful for ameliorating or treating proliferative, inflammatory skin diseases. An example of such compounds are the hypolipidemic fibrates. Examples of these compounds are clofibrate, fenofibrate, bezofibrate, ciprofibrate and gemfibrozil.

Lambe, K. G., Tugwood, J. D. "A human peroxisome-proliferator-activated receptor-gamma is activated by inducers of adipogenesis, including thiazolidinedione drugs," *Eur. J. Biochem.* 239(1):1–7, Jul. 1, 1996 which is incorporated herein by reference.

Hypolipidemic fibrates are also known as aryloxalkanoic acid derivatives and are described in U.S. Pat. Nos. 5,712, 396 and 5,719,197 which are incorporated herein by reference.

A method for synthesizing libraries of biased compounds designed to be activators of PPARγ and its isotypes (e.g., PPARδ) has been published, and can be used to create novel non-thiazolidinedione, non-prostaglandin, non-fatty acid PPARγ activators. Brown, P. J., Smith-Oliver, T. A., Charifson, P. S., Tomkinson, N. C., Fivush, A. M., Sternbach, D. D., Wade, L. E., Orband-Miller, L., Parks, D. J., Blanchard, S. G., Kliewer, S. A., Lehmann, J. M., Willson, T. M. "Identification of peroxisome proliferator-activated receptor ligands from a biased chemical library," *Chem. Biol.* 4(12):909–918, December 1997 which is incorporated herein by reference.

Using a method of the invention, therapeutic compounds are typically administered to human patients topically or orally. Parenteral administration is used in appropriate circumstances apparent to the practitioner. Preferably, the compositions are administered in unit dosage forms suitable for single administration of precise dosage amounts.

To prepare a topical formulation, a therapeutically effective concentration of the compound is placed in a dermatological vehicle as is known in the art. The amount of the therapeutic compound to be administered and the compound's concentration in the topical formulations depend upon the vehicle selected, the clinical condition of the patient, the side effects and the stability of the compound in the formulation. Thus, the physician employs the appropriate preparation containing the appropriate concentration of the therapeutic compound and selects the amount of formulation administered, depending upon clinical experience with the patient in question or with similar patients.

The concentration of the therapeutic compound for topical formulations is in the range of about 1 mg/ml to about 1000 mg/ml. Typically, the concentration of the therapeutic compound for topical formulations is in the range of about 2.5 mg/ml to about 25 mg/ml. Solid dispersions of the therapeutic compound as well as solubilized preparations can be used. Thus, the precise concentration is subject to modest experimental manipulation in order to optimize the therapeutic response. About 2,500 mg of therapeutic compound per 100 grams of vehicle is useful in the treatment of skin lesions to provide a 2.5% weight/weight (w/w) formulation. Suitable vehicles include oil-in-water or water-in-oil emulsions using mineral oils, petrolatum and the like as well as gels such as hydrogel.

Alternative topical formulations include shampoo preparations, oral paste, and mouth wash preparations. ORABASE® can be used as the base oral paste to which the therapeutic compound is added. Concentrations of therapeutic compound are typically as stated above for topical formulations.

The therapeutic compound is optionally administered topically by the use of a transdermal therapeutic system (see Barry, Dermatological Formulations, (1983) p. 181 and literature cited therein). While such topical delivery systems have been designed largely for transdermal administration of low molecular weight drugs, by definition they are capable of percutaneous delivery. They may be readily adapted to administration of the therapeutic compounds of the invention by appropriate selection of the rate-controlling microporous membrane.

For ophthalmic applications, such as treatment of keratitis, the therapeutic compound is formulated into solutions, suspensions, and ointments appropriate for use in the eye. The concentrations are usually as discussed above for topico-local preparations. For ophthalmic formulations, see Mitra (ed.), Ophthalmic Drug Delivery Systems, Marcel Dekker, Inc., New York, N.Y. (1993) and also Havener, W. H., Ocular Pharmacology, C.V. Mosby Co., St. Louis (1983).

The therapeutic compound is alternatively administered by aerosol. This is accomplished by preparing an aqueous aerosol, liposomal preparation or solid particles containing the compound. A nonaqueous (e.g., fluorocarbon propellent) suspension could be used. Sonic nebulizers are preferred because they minimize exposing the therapeutic compound to shear, which can result in degradation of the compound.

Ordinarily, an aqueous aerosol is made by formulating an aqueous solution or suspension of the therapeutic compound together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

For oral administration, either solid or fluid unit dosage forms can be prepared. For preparing solid compositions such as tablets, the compound of interest is mixed into formulations with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound of interest with an inert pharmaceutical diluent and filling the mixture into a hard gelatin capsule of appropriate size. Soft gelatin capsules are prepared by machine encapsulation of a slurry of the compound of interest with an acceptable vegetable oil, light liquid petrolatum or other inert oil. Fluid unit dosage forms for oral administration such as syrups, elixirs and suspensions can be prepared. The water soluble forms can be dissolved in an aqueous vehicle together with sugar, aromatic flavoring agents and preservatives to form a syrup. An elixir is prepared by using a hydroalcoholic (e.g., ethanol) vehicle with suitable sweeteners such as sugar and saccharin, together with an aromatic flavoring agent. Suspensions can be prepared with an aqueous vehicle with the aid of a suspending agent such as acacia, tragacanth, methylcellulose and the like. Appropriate formulations for parenteral use are apparent to the practitioner of ordinary skill. Usually, the therapeutic compound is prepared in an aqueous solution (discussed below) in a concentration of from about 1 to about 100 mg/ml. More typically, the concentration is from about 10 to 60 mg/ml or about 20 mg/ml. The formulation, which is sterile, is suitable for various parenteral routes including intra-dermal, intraarticular, intramuscular, intravascular, and subcutaneous.

In addition to the therapeutic compound, the compositions may include, depending on the formulation desired, pharmaceutically-acceptable, non-toxic carriers or diluents, which include vehicles commonly used to form pharmaceutical compositions for animal or human administration. The diluent is selected so as not to unduly affect the biological activity of the combination. Examples of such diluents which are especially useful for injectable formulations are water, the various saline solutions, Ringer's solution, dextrose solution, and Hank's solution. In addition, the pharmaceutical composition or formulation may include additives such as other carriers; adjuvants; or nontoxic, nontherapeutic, nonimmunogenic stabilizers and the like.

Furthermore, excipients can be included in the formulation. Examples include cosolvents, surfactants, oils, humectants, emollients, preservatives, stabilizers and antioxidants. Any pharmacologically acceptable buffer may be used, e.g., tris or phosphate buffers. Effective amounts of diluents, additives and excipients are those amounts which are effective to obtain a pharmaceutically acceptable formulation in terms of solubility, biological activity, etc.

The term "unit dosage form" refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the unit dosage forms of this invention are dictated by and dependent on (a) the unique characteristics of the active material and the particular effect to be achieved and (b) the limitations inherent in the art of compounding such an active material for use in humans and animals. Examples of unit dosage forms are tablets, capsules, pills, powder packets, wafers, suppositories, granules, cachets, teaspoonfuls, tablespoonfuls, dropperfuls, ampoules, vials, aerosols with metered discharges, segregated multiples of any of the foregoing, and other forms as herein described.

Thus, a composition of the invention includes a therapeutic compound which may be formulated with conventional, pharmaceutically acceptable, vehicles for topical, oral or parenteral administration. Formulations may also include small amounts of adjuvants such as buffers and preservatives to maintain isotonicity, physiological and pH stability. Means of preparation, formulation and administration are known to those of skill. See generally Remington's Pharmaceutical Science 15th ed., Mack Publishing Co., Easton, Pa. (1980).

Slow Release Delivery.

Slow or extended-release delivery systems, including any of a number of biopolymers (biological-based systems), systems employing liposomes, and polymeric delivery systems, can be utilized with the compositions described herein to provide a continuous or long term source of therapeutic compound. Such slow release systems are applicable to formulations for topical, ophthalmic, oral, and parenteral use.

Routes of Administration.

Therapeutic agents of the invention are usually delivered or administered topically or by transdermal patches for treating dermal psoriasis. Alternatively, oral administration is used. Additionally, the agents can be delivered parenterally, especially for treatment of arthritis, such as psoriatic arthritis, and for direct injection of skin lesions. Parenteral therapy is typically intra-dermal, intra-articular, intramuscular or intravenous.

A preferred way to practice the invention is to apply the compound of interest, in a cream, lotion, ointment, or oil based carrier, directly to the skin lesions. Typically, the concentration of therapeutic compound in a cream, lotion, or oil is 1–2%. Alternatively, an aerosol can be used topically. These compounds can also be orally administered.

In general, the preferred route of administration is topical (including administration to the eye, scalp, and mucous membranes), oral, or parenteral. Topical administration is preferred in treatment of skin lesions, including lesions of the scalp, lesions of the cornea (keratitis), and lesions of mucous membranes where such direct application is practical. Shampoo formulations are sometimes advantageous for treating scalp lesions such as seborrheic dermatitis and psoriasis of the scalp. Mouthwash and oral paste formulations can be advantageous for mucous membrane lesions, such as oral lesions and leukoplakia. Oral administration is a preferred alternative for treatment of skin lesions and other lesions discussed above where direct topical application is not as practical, and it is a preferred route for other applications.

Intra-articular injection is a preferred alternative in the case of treating one or only a few (such as 2–6) joints. Usually, the compound is delivered in an aqueous solution of about 10–20 mg/ml. Additionally, the therapeutic compounds are injected directly into lesions (intra-lesion administration) in appropriate cases. Intradermal administration is an alternative for dermal lesions such as those of psoriasis.

Dosage and Schedules.

An effective quantity of the compound of interest is employed in treatment. The dosage of compounds used in accordance with the invention varies depending on the compound and the condition being treated. The age, weight, and clinical condition of the recipient patient; and the: experience and judgment of the clinician or practitioner administering the therapy are among the factors affecting the selected dosage. Other factors include the route of administration the patient, the patient's medical history, the severity of the disease process, and the potency of the particular compound. The dose should be sufficient to ameliorate symptoms or signs of the disease treated without producing unacceptable toxicity to the patient.

Broadly, an oral dosing schedule is from about 100 to about 600 mg twice a day. More typically, a single dose is about 100–200 mg of compound given twice a day. A convenient oral dose for an adult patient is 200 mg twice a day. A dosage range for topical treatment is about 0.1% to about 10% (weight/volume) in a cream or ointment, applied twice a day. A usual dose for intra-articular injection is 20–40 mg injected per joint, not generally exceeding three joints per therapy session. A typical dosage for intra-dermal administration is about 20–75 mg per injection per site.

Typically, the dosage is administered at least once a day until a therapeutic result is achieved. Preferably, the dosage is administered twice a day, but more or less frequent dosing can be recommended by the clinician. Once a therapeutic result is achieved, the drug can be tapered or discontinued. Occasionally, side effects warrant discontinuation of therapy. In general, an effective amount of the compound is that which provides either subjective relief of symptoms or an objectively identifiable improvement as noted by the clinician or other qualified observer.

The foregoing is offered primarily for purposes of illustration. It will be readily apparent to those of ordinary skill in the art that the operating conditions, materials, procedural steps and other parameters of the system described herein may be further modified or substituted in various ways without departing from the spirit and scope of the invention. For example, the invention has been described with human patients as the usual recipient, but veterinary use is also contemplated. Thus, the invention is not limited by the preceding description, but rather by the appended claims. All cited literature is incorporated by reference.

EXAMPLES

Example 1

HUMAN KERATINOCYTES EXPRESS MESSENGER RNA AND PROTEIN FOR PPARγ

Human keratinocytes were grown in 35 mm dishes using standard cell culture techniques familiar to those skilled in the art. The cells were washed with phosphate buffered saline (PBS) followed by fixation for 10 minutes in 4% paraformaldehyde (in PBS). Following washes in PBS, cells were permeabilized with ice cold methanol for 2 minutes followed by three washes with PBS. Fixed cells were blocked for one hour with 5% sheep serum in PBS followed by incubation for 1 hr at room temperature and overnight at 4° in the primary antibody against PPARγ diluted in PBS containing 0.2% BSA. The antibody against PPARγ was purchased from Affinity BioReagents, Inc.; the antibody was produced by immunizing rabbits with a 15 residue synthetic peptide derived from a mouse sequence that is highly conserved for both subtypes of PPARγ but exhibits no significant homology with other forms of PPAR. Following three washes in PBS, cells were incubated with FITC sheep anti-rabbit IgG and incubated in the dark for one hour. Cells were washed with PBS, mounted in Vectashield and viewed by phase contrast and epifluorescence microscopy. Human keratinocytes were cultured in serum free media and then incubated with an antibody specific for PPARγ (both the $\gamma_1$ and $\gamma_2$ subtypes).

Figure 1:
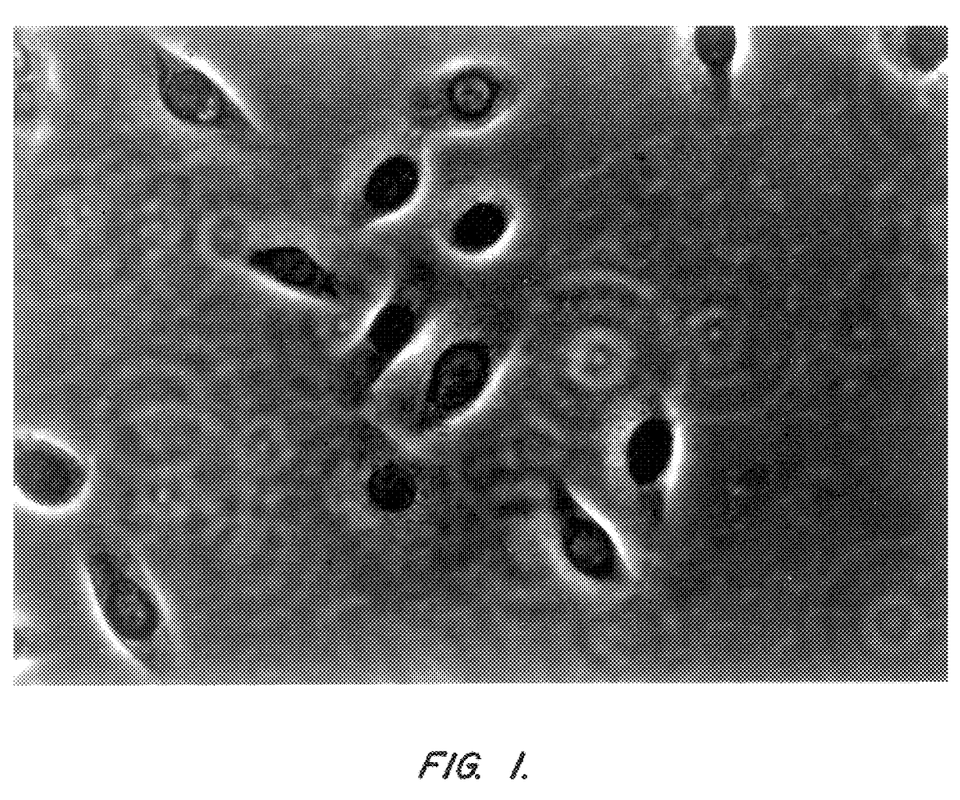
FIG. 1. Phase contrast micrograph (20× magnification) of cultured human keratinocytes incubated with rabbit antibody to PPARγ and FITC labeled anti rabbit IgG antibody (as described in Example 1).
Figure 2:
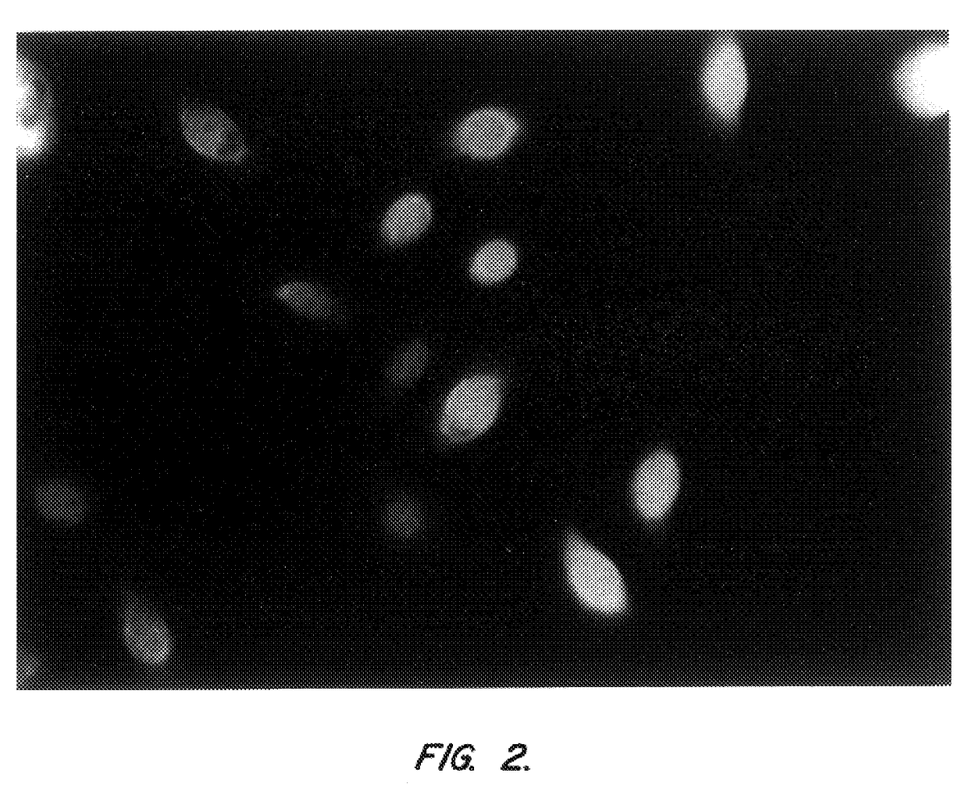
FIG. 2. Epifluorescence micrograph (20× magnification) of the same human keratinocytes described in FIG. 1 and Example 1 showing intense immunofluorescent nuclear staining due to presence of PPARγ protein.
Figure 3:
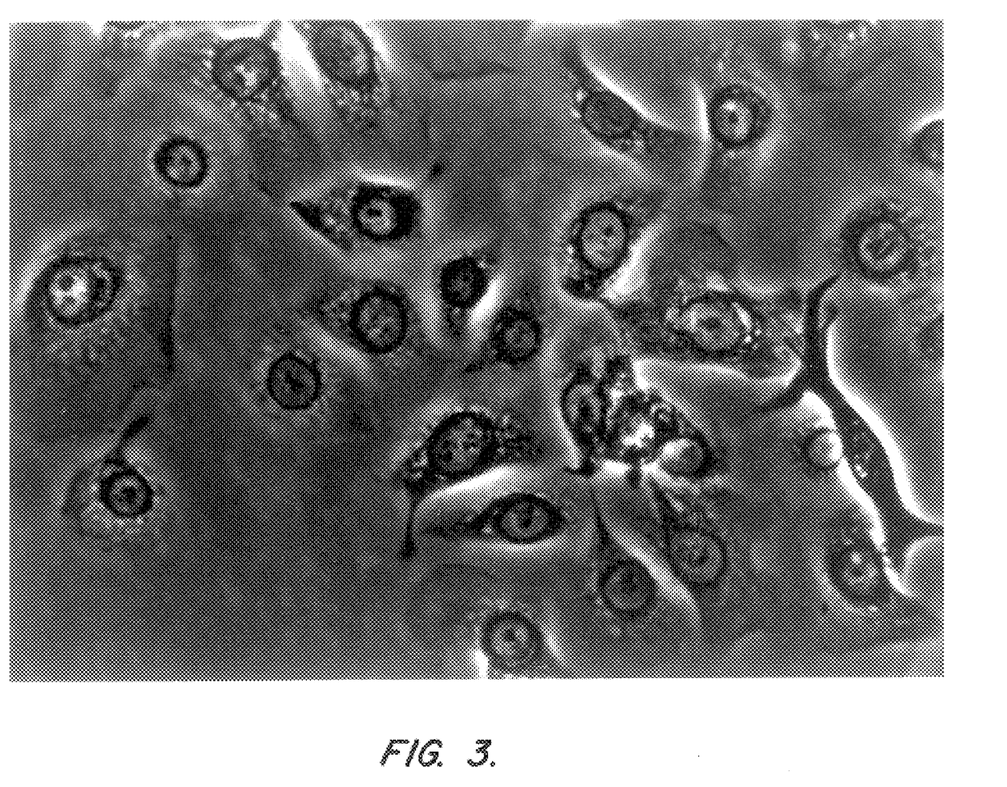
FIG. 3. Phase contrast image (20× magnification) of human keratinocytes from control experiments in which the keratinocytes were not incubated with antibody to PPARγ.
Figure 4:
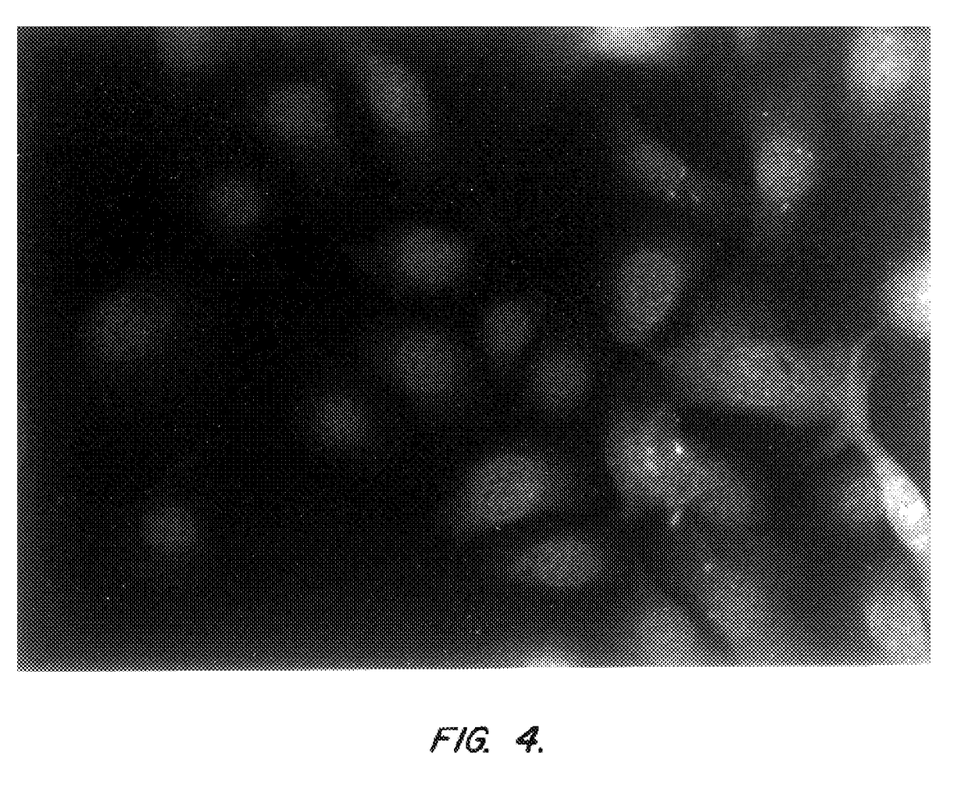
FIG. 4. Epifluorescence micrograph (20× magnification) of the same human keratinocytes described in FIG. 3 showing little or no immunofluorescent nuclear staining. The lack of immunofluorescent staining in the control experiments indicates that the positive staining results in FIG. 2 are due to the presence of PPARγ rather than nonspecific immunofluorescence.

FIG. 1 shows a phase contrast micrograph (20×) of human keratinocytes treated as described above. FIG. 2 shows the same human keratinocytes viewed by epifluorescence microscopy and reveals intense immunofluorescent nuclear staining demonstrating the presence of PPARγ. FIGS. 3 and 4 how phase contrast and epifluorescent images respectively of human keratinocytes from control experiments in which the keratinocytes were not incubated with antibody to PPARγ. The lack of immunofluorescent staining in the control experiments indicates that the positive staining results in FIG. 2 are due to the presence of PPARγ rather than nonspecific immunofluorescence.

Messenger ribonucleic acid (RNA) was prepared from cultured human keratinocytes using standard methods known to those skilled in the art and then reverse transcribed to cDNA using the Superscript cDNA synthesis kit as described by the manufacturer (Life Technologies, Inc., Gibco BRL, Gaithersburg, Md.). Oligonucleotide primers were designed according to published DNA sequences for the peroxisome proliferator activated receptor. The primers allowed for amplification of portions of the cDNAs encoding the $\gamma_1$ and $\gamma_2$ subtypes of the peroxisome proliferator activated receptor using polymerase chain reaction (PCR) techniques commonly used by those skilled in the art. The oligonucleotide primers were used to amplify cDNA obtained from human keratinocytes and the resultant PCR products were analyzed by polyacrylamide gel electrophoresis using standard methods familiar to those skilled in the art. The upstream primer sequence was 5' acc atg gtt gac aca gag atg 3' and the downstream primer sequence was tgt aat ctg caa cca ctg gat. A distinct PCR amplification target of the predicted size for PPARγ$_1$ was detected after 30 cycles of PCR. Primers specific for PPARγ$_2$ were subsequently tested and yielded a faint band of the predicted size (upstream primer sequence was ggt gaa act ctg gga gat tct; downstream primer sequence was tgt aat ctg caa cca ctg gat). Thus, reverse-transcriptase-PCR amplification studies of messenger RNA from human keratinocytes yielded DNA products of a size expected for both the $\gamma_1$ and $\gamma_2$ subtypes of the peroxisome proliferator activated receptor. These results indicate the presence of messenger RNA encoding both the $\gamma_1$ and $\gamma_2$ subtypes of the peroxisome proliferator activated receptor in human keratinocytes.

Example 2

A COMPOUND THAT MODIFIES THE ACTIVITY OF PPARγ INHIBITS THE PROLIFERATION OF HUMAN KERATINOCYTES

Cell lines transfected with a cDNA construct encoding PPARγ have been shown to express functionally active peroxisome proliferator activated receptors. In studies using such cell lines, it has been demonstrated that the thiazolidinedione troglitazone significantly activates PPARγ. This example demonstrates that a compound that activates PPARγ (troglitazone) is useful for inhibiting proliferation of keratinocytes. The use of proliferating human keratinocytes in culture as a test system for determining the utility of a compound for treating hyperproliferative and inflammatory disorders of the skin is well documented (Kitanot et at., Euro. J Clin. Investig. 21:53–58 (1991) and West, et at., J. Investigative Derm. 99(1):95–100 (1992).)

Figure 5:
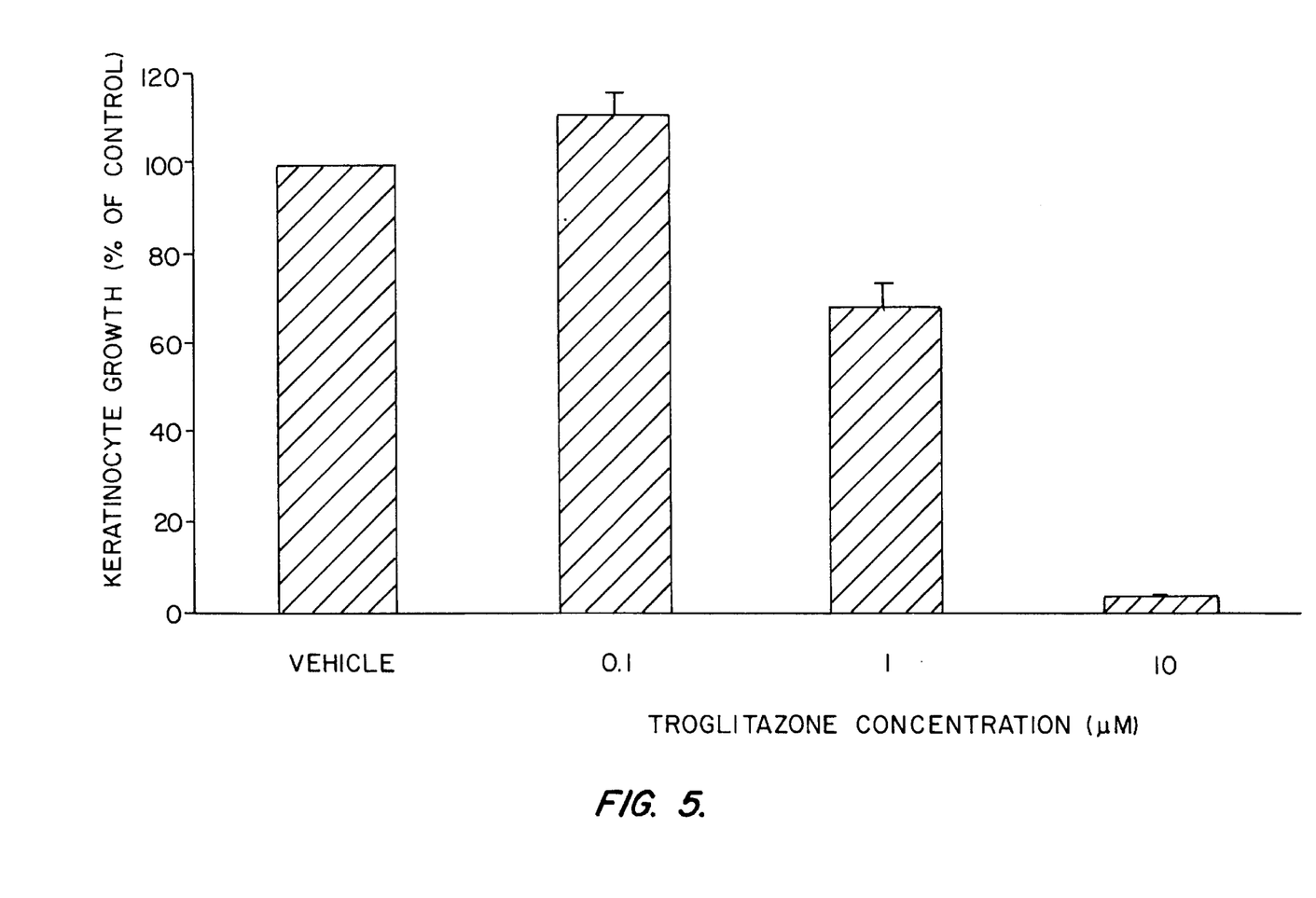
FIG. 5. Bar graph showing the inhibitory effect of troglitazone on the proliferation of keratinocytes from 3 adult human subjects. The antiproliferative effect of troglitazone in human keratinocytes was dose-dependent and saturable (IC50•2.1:μmol/L).

Adult human keratinocytes, obtained by keratome biopsy, were cultured in low calcium, serum free media (MCDB, see Boyce, B. A. and R. G. Ham, J. Investigative Derm. 81(1) :335–405 (July 1983)) in the presence of each of the following: vehicle (0.1% dimethyl sulfoxide (DMSO)), 0.1 μM, 1.0 μ, and 10 μM troglitazone for 4 days. Cell number was assessed at time zero (before treatment) and at the end of the treatment period by the neutral red dye assay. See Kitano, et at., Euro. J. Clin. Investig. 21:53–58 (1991) and West, et at., J. Investigative Derm. 99(1):95–100 (1992). Each condition was performed in 12 replicates, on keratinocytes from three subjects and the results were combined from the three subjects. Data displayed are means +/− standard errors in FIG. 5. The coordinate plots the cell growth of the keratinocytes as the percentage of controls. The ordinate plots the micromolar concentration of the therapeutic compound, troglitazone. As demonstrated by the data, application of troglitazone to keratinocytes taken from human adults results in a dose response inhibition of cell growth. Specifically, the proliferation of the skin cells in culture was inhibited in a dose dependent fashion by the application of troglitazone.

Example 3

A CLINICAL TRIAL, TOPICAL THERAPY OF PSORIASIS

A patient having dermal manifestations of psoriasis is selected for therapy using the invention. A compound known to modify the activity PPARγ such as a prostaglandin J2 compound is prepared in a cream vehicle at a concentration of 2% (weight/volume) and is applied to the affected skin three times a day. After the skin lesions have subsided, therapy is discontinued.

Example 4

ACTIVATION OF PPARγ INHIBITS THE GROWTH OF HUMAN KERATINOCYTES

Inhibition of proliferating human keratinocytes in culture have been utilized as a system for screening and identifying potential therapeutic agents such as vitamin D derivatives (Kitano et at., 1991) and retinoids (West et at., 1992), for the treatment of inflammatory, proliferative skin diseases (e.g., psoriasis vulgaris, acne vulgaris, hidradenitis suppurativa).

The prediction that PPARγ activators are efficacious in the treatment of inflammatory, proliferative skin diseases is not obvious. Previously, Wahli et at. (1995) screened various tissues from the rat for the presence of PPARγ, including skin, and concluded that PPARγ is not expressed in mammalian vertebrate (rodent) skin. Except for data presented herein, the expression of PPARγ mRNA or receptor protein in human keratinocytes have not been previously demonstrated.

Thiazolidinediones bind and activate the peroxisome proliferator-activated receptor-γ (PPARγ). The cyclopentenone prostaglandins, including prostaglandins in the J2 (e.g., 15-deoxy-Δ-PG J2) and A1 series activate PPARγ to varying degrees, but are structurally dissimilar to the thiazolidinediones. The data shown below demonstrates that the cyclopentenone prostaglandin, 15-deoxy-A-12,14-prostaglandin J2 (15-deoxy-PG J2), a metabolite of prostaglandin D2 inhibits the proliferation of human keratinocytes in culture.

DETERMINATION OF PROLIFERATION

Human keratinocytes were obtained from Clonetics (San Diego, California) and subcultured into a proprietary (Clonetics) medium optimized for cell growth and maintenance. Proliferation of keratinocytes was determined using MTS, 3-(4,5-dimethylthiazol-2-yl)-5-(3-carboxymethoxyphenyl)-2-(4-sulfophen 1)-2H-tetrazolium (PMS/MTS) as described in the CellTiter 96 AQueous Non-Radioactive Cell Proliferation Assay (Promega Inc.). Only viable cells reduce MTS to the soluble formazan, and viable cell numbers correlate with optical density (Cory et at., 1991).

Cells were seeded at 2 to $4 \times 10_4$ cells/ml of growth medium in 24 well microtiter plates. Twenty-four hours post-plating cells were treated with vehicle alone (0.1% DMSO) or various concentrations of 15-deoxy-PG J2 was added to each well (quadruplicate samples per concentration) for an additional 4 days. At each time point 100 ul of the PMS/MTS assay mix is added and absorbance at 490 nm was recorded four hours later with a microplate spectrophotometer (BioTek Instrument Co).

RESULTS

Addition of 15-deoxy-PG J2 to the cultured keratinocytes resulted in a dose-dependent inhibition of proliferation (Table 1). The concentration for half-maximal inhibition of growth (IC50) was approximately 4 $\mu$M.

TABLE 1

INHIBITORY EFFECT OF 15-DEOXY-PG J2 ON PROLIFERATION OF HUMAN KERATINOCYTES

| [15-deoxy-PG J2] (uM) | % inhibition |
| --- | --- |
|  | 5 |
| 2 | 22 |
| 4 | 51 |
| 8 | 76 |
| 20 | 100 |

REFERENCES

1. Kitano, Y., Ikeda, N., Okano, M.: "Suppression of proliferation of human epidermal keratinocytes by 1,25-dihydroxyvitamin D3. Analysis of its effect on psoriatic lesion and of its mechanism using human keratinocytes in culture." *Eur. J. Clin. Invest.* 21:53–58, 1991.
2. West, M. R., Page, J. M., Turner, D. M., Wood, E. J., Holland, D. B., Cunliffe, W. J, Rupniak, H. T.: "Simple assays of retinoid activity as potential screens for compounds that may be useful in treatment of psoriasis." *J. Invest. Dermatol.* 99:95–100, 1992.
3. Lemberger, T., Braissant, O, Juge-Aubry, C., Keller, H., Saladin, R., Staels, B., Auwerx, J., Burger, A. G., Meier, C. A., Wahl, W. "PPAR tissue distribution and interactions with other hormone-signaling pathways." *Ann. N.Y. Acad. Sci.* 804:231–251, 1996.
4. Cory, A. H., Owen, T. C., Baretrop, J. A., Cory, J. G. "Use of an aqueous soluble tetrazoliuml formazan assay for cell growth assays in culture." *Cancer Commun.* 3:207–212, 1991.

Example 5

A CLINICAL TRIAL, TOPICAL THERAPY OF ACNE VULGARIS

A patient having dermal manifestations of acne vulgaris is selected for therapy using the invention. A compound known to modify the activity of PPARy such as prostaglandin J2 is prepared in a cream vehicle at a concentration of 2% (weight/volume) and is applied to the affected skin three times a day. After the skin lesions have subsided, therapy is discontinued.

Example 6

A CLINICAL TRIAL, ORAL THERAPY OF PSORIASIS

A patient having psoriasis afflicting multiple areas of the skin as well as the nails and scalp is selected for therapy. The patient weighs 80 kilograms and, other than the psoriasis, enjoys good health. The patient is given a pregnancy test to confirm that the patient is not pregnant. Provided that the patient is not pregnant and does not plan to become pregnant during treatment, a compound that modifies the activity of PPARγ such as a prostaglandin J2 analog is orally administered in a dosage of 200 milligrams twice a day. The patient is monitored for improvement in his manifestations of psoriasis. Additionally, a complete blood count, including white cell count and differential, a platelet count, and liver function tests (such as levels of alkaline phosphatase, lactose dehydrogenase, and transaminases) are checked prior to treatment and periodically thereafter. The dosage is tapered and discontinued when the manifestations of psoriasis subside.

Example 7

A CLINICAL TRIAL, ORAL THERAPY OF ACNE VULGARIS

A patient having acne vulgaris affecting multiple areas of the face and upper back is selected for therapy. The patient weighs 70 kilograms and, other than having acne vulgaris, enjoys good health. The patient is given a pregnancy test to confirm that the patient is not pregnant. Provided that the patient is not pregnant and does not plan to become pregnant during treatment, a compound that modifies the activity of PPARγ such as a prostaglandin J2 analog is orally administered in a dosage of 200 milligrams twice a day. The patient is monitored for improvement in his or her manifestations of acne vulgaris. Additionally, a complete blood count, including white cell count and differential, a platelet count, and liver function tests (such as levels of alkaline phosphatase, lactose dehydrogenase, and transaminases) are checked prior to treatment and periodically thereafter. The dosage is tapered and discontinued when the manifestations of psoriasis subside.

Example 8

A CLINICAL TRIAL, INTRA-DERMAL ADMINISTRATION

A patient having psoriasis is treated with intra-dermal injection of a compound that modifies the activity of PPARγ such as a prostaglandin J2 analog in 20 mg/ml aqueous solution. About 20–75 mg are injected directly into each site or dermal lesion treated. The therapy is repeated weekly until the injected lesions diminish or vanish.

What is claimed is:

1. A method of inhibiting a disease of mammalian skin involving proliferation of keratinocytes wherein the method comprises administering an amount of a compound able to activate keratinocyte peroxisome proliferator activated receptors in an amount sufficient to inhibit proliferation of keratinocytes, with the proviso that the compounds not be thiazolidine nor fatty acids nor prostaglandins.

2. A method of claim 1 wherein the skin is human.

3. A method of claim 1 wherein the disease is psoriasis.

4. A method of claim 1 wherein the disease is acne vulgaris.

5. A method of claim 1 wherein the compound is a hypolipidemic fibrates.

6. A method of claim 1 wherein the compound is selected from the group consisting of clofibrate, fenofibrate, bezofibrate, ciprofibrate and gemfibrozil.

* * * * *